United States Patent [19]

Jarby

[11] 4,365,162

[45] Dec. 21, 1982

[54] DEVICE FOR HOLDING X-RAY-SENSITIVE FILMS FOR ODONTOLOGICAL RADIOGRAPHS

[76] Inventor: Sven Jarby, Postfach 38, CH-9470 Buchs SG, Switzerland

[21] Appl. No.: 120,756

[22] Filed: Feb. 12, 1980

[30] Foreign Application Priority Data

Mar. 9, 1979 [CH] Switzerland ............. 2292/79

[51] Int. Cl.³ ............................ G03B 41/16
[52] U.S. Cl. .................................. 378/170
[58] Field of Search .................. 250/478, 479

[56] References Cited

U.S. PATENT DOCUMENTS

| | | |
|---|---|---|
| 1,405,217 | 1/1922 | Houser . |
| 1,467,850 | 9/1923 | Hall . |
| 1,906,223 | 5/1933 | Buck . |
| 1,923,669 | 8/1933 | Harrison ............ 250/479 |
| 1,947,014 | 2/1934 | Levy . |
| 2,090,933 | 8/1937 | Bolin . |
| 3,092,721 | 6/1963 | Medwedeff et al. ........ 250/479 |
| 3,356,845 | 12/1967 | Bergendal . |
| 3,473,026 | 10/1969 | Updegrave ............ 250/479 |
| 4,048,506 | 9/1977 | Updegrave ............ 250/479 |
| 4,057,732 | 11/1977 | Klauser ............ 250/479 |

FOREIGN PATENT DOCUMENTS 548769 3/1974 Switzerland .

Primary Examiner—Davis L. Willis
Attorney, Agent, or Firm—Benoit Law Corporation

[57] ABSTRACT

Figure 2:
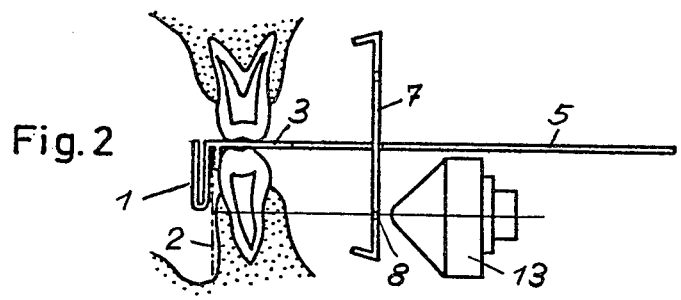
Figure 3:
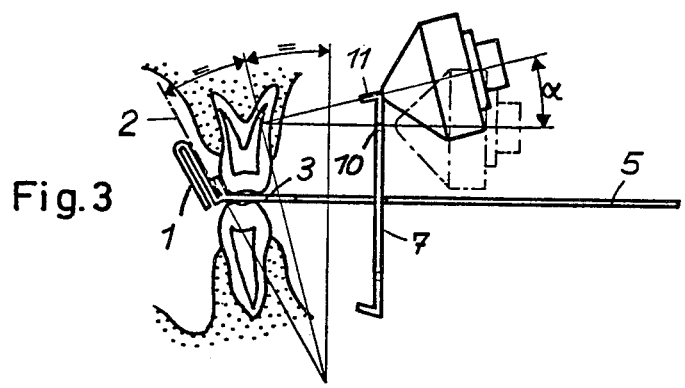
Figure 4:
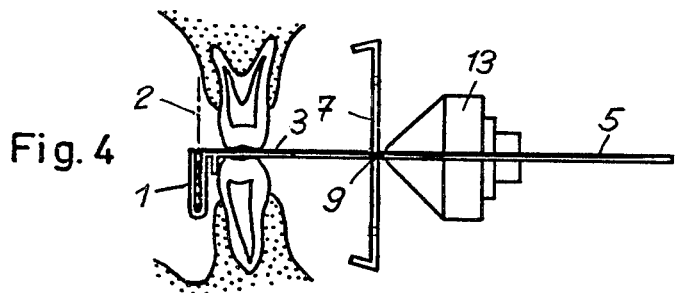

A device (1) for holding X-ray film (2) during the taking of radiographs of patients' teeth with X-rays emanating from a cone (13) of an X-ray source has a bite wing (3) extending in a horizontal center plane perpendicularly to an X-ray film plane, for retention of the device by patients' teeth. An X-ray film holder is carried by the bite wing for retaining X-ray film centered relative to the horizontal center plane and alternatively vertically offset from that horizontal center plane. A guide rod (5) is connected laterally to the bite wing and extends in the horizontal center plane perpendicularly away from the X-ray plane, for guidance of X-ray cone. An aiming rod (7) extends in a vertical center plane of the centered and the vertically offset X-ray film. A transverse rod (6) extends in the horizontal center plane from the guide rod to the aiming rod, for mounting that aiming rod (7) at a distance from the bite wing. The aiming rod (7) is equipped for an aiming of the X-ray cone at an intersection of the horizontal and vertical center planes on the centrally retained X-ray film in the taking of radiographs of at least the crowns of upper and lower teeth (FIG. 4). The aiming rod (7) is also equipped for an aiming of the X-ray cone at an intersection of horizontal and vertical center lines of the vertically offset X-ray film in the taking of radiographs of root portions of the teeth (FIGS. 2 and 3).

9 Claims, 6 Drawing Figures

U.S. Patent   Dec. 21, 1982   Sheet 1 of 2   4,365,162

DEVICE FOR HOLDING X-RAY-SENSITIVE FILMS FOR ODONTOLOGICAL RADIOGRAPHS

The present invention relates to a device for holding X-ray-sensitive films for odontological radiographs in accordance with the pre-characterising clause of the Main Patent Claim.

When examining the teeth, namely the crown and the root, the points of interest are, as is known, subjected to radioscopy by means of X-rays and the X-ray image is recorded on a film. Customarily, the patient is asked to hold the film, with a finger, against the gingiva on the side of the gums or on the side of the tongue. Thus, changes in the region of the root of the teeth can very readily be detected. This procedure fails, however, when it is intended to detect cavities or cracks in the crowns and/or to discern the biting position of the teeth.

Accordingly, several devices for holding the films have already been disclosed. It is common to all of them that, to a holder for the film, a bite holding is fastened, by means of which the patient firmly holds the film at a defined place by biting the teeth together. For example, an adhesive band, the ends of which, after it has been folded in the middle, can be stuck to the film, is obtainable on the market under the name "UNI-FIX". The patient clamps the wing thus formed between the upper and lower teeth and thus holds the film in place. By fixing the point of adhesion on the film, the dentist can determine which part of the set of teeth is to be photographed. This is of course a useful expedient, but it is always questionable whether the developed film image indeed represents the desired part. If this is not the case, the procedure must be repeated during a further appointment, and this can be inconvenient for both parties.

U.S. Pat. No. 3,356,845 shows a further embodiment of a film holder having two holders for different positions of the film, on the one hand for depicting the crowns, and for depicting the upper and lower root parts. A bite wing in the form of a perforated plate is present on the film holder. The perforation serves to improve the grip between the teeth and the bite wing. A hinge-like joint between the bite wing and the film holder makes it possible to place the film holder at an angle so that it can adapt to the curvature on the transition from the gingiva to the gums.

A further form of a film holder is described in U.S. Pat. No. 4,057,732. A guide rod for aligning the cone or the tube of an X-ray source is located on a clamp for clamping the film, in an arrangement perpendicular to the plane of the film. At the transition point between the clamp and the guide rod there is a bite wing in the form of a widening of the guide rod. At a distance from the clamp, a transverse rod branches off the guide rod in a direction parallel to the plane of the film. This transverse rod is in the same plane as that determined by the bite wing. The transverse rod is provided with markings which serve to align the tip of the cone or the edge of the tube of the X-ray source to the point of intersection of the horizontal and vertical centre lines of the film. A disadvantage of this embodiment of a film holder is the fact that the film is held in the mouth in only one single position, namely for depicting the crowns of the teeth, and the X-ray is thus aligned only in the biting plane to the vertical centre line of the film. Nevertheless, this film holder has an advantage compared with those described earlier since, in the case of the latter, there is no possibility of alignment relative to the film and a check with regard to the precise position of the film is likewise impossible.

It is, accordingly, the object of the invention to provide a film holder for odontological radiographs, with which it is possible to adjust the position of the film from outside the mouth to various objects to be depicted, such as roots and/or crowns, and to align the X-ray to the centre of the film in any of the distinct positions.

According to the invention, a device for holding X-ray film during the taking of radiographs of patients' teeth with X-rays emanating from a cone of an X-ray source, comprises, in combination, a bite wing extending in a horizontal center plane perpendicularly to an X-ray film plane, for retention of the device by patients' teeth, an X-ray film holder carried by the bite wing and including means for retaining X-ray film centered relative to the horizontal center plane and alternatively vertically offset from the horizontal center plane, a guide rod connected laterally to the bite wing and extending in the horizontal center plane perpendicularly away from the X-ray plane, for guidance of the X-ray cone, an aiming rod extending in a vertical center plane of the centered and the vertically offset X-ray film, a transverse rod extending in the horizontal center plane from the guide rod to the aiming rod, for mounting the aiming rod at a distance from the bite wing, first means at the aiming rod for aiming the X-ray cone at an intersection of the horizontal and vertical center planes on the centrally retained X-ray film in the taking of radiographs of at least the crowns of upper and lower teeth, and second means on the aiming rod for aiming the X-ray cone at an intersection of horizontal and vertical center lines of the vertically offset X-ray film in the taking of radiographs of root portions of the teeth.

Figure 1:
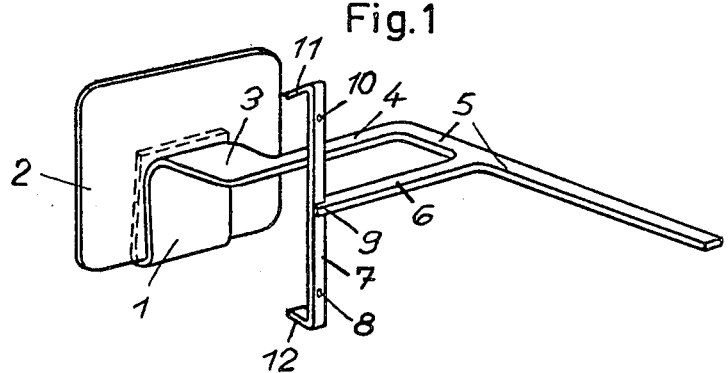
Figure 5:
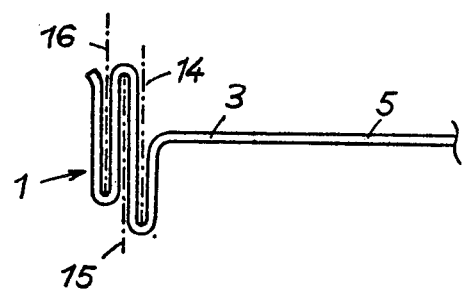
Figure 6:
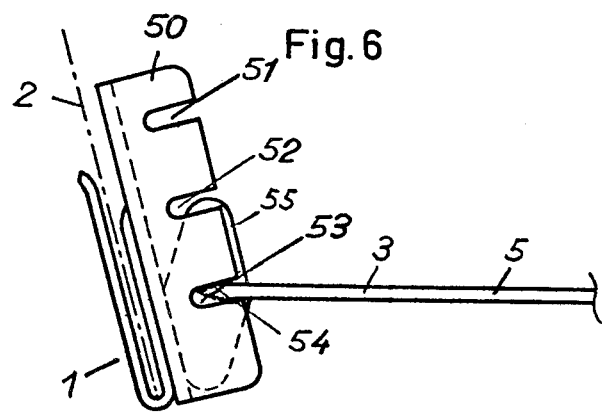

Illustrative embodiments of the invention and their use are described in the following text by reference to the drawing in which:

FIG. 1 shows a perspective view of a device according to the invention with a film in a middle position, FIG. 2 shows a lateral elevation of an embodiment for holding the film in two different positions when depicting the roots of the lower teeth by means of an X-ray cone, FIG. 3 shows a lateral elevation similar to that in FIG. 2, but when depicting the roots of the upper teeth, with the film holder tilted relative to the vertical by a certain angle, FIG. 4 shows a lateral elevation similar to that in FIG. 2 for depicting the crowns of the upper and lower teeth, FIG. 5 shows a lateral elevation of the part of the device having the film holder, in an embodiment for holding a film in three different positions, and FIG. 6 shows a perspective view of the part of the device having the film holder, in a further embodiment in which the entire film holder can be adjusted to different positions.

The device according to the invention in FIG. 1 consists of a film holder 1 in the form of a clamping bracket with a film 2 which is customarily used for odontological radiographs and the dimensions of which are 45 mm wide, 30 mm high and about 1.5 mm thick, in the use position for depicting the crowns of the teeth. In the horizontal centre plane perpendicular to the plane of the film, there is a bite wing 3 adjoining the film holder. The bite wing 3 is adjoined by a first transverse rod 4 which likewise lies in the centre plane defined above and is in an arrangement parallel to the plane of the film. Likewise in the centre plane, this is then followed by a guide rod 5 which points perpendicularly away from the plane of the film. At a distance from the first transverse rod 4 and parallel thereto, a second transverse rod 6 branches off the guide rod 5. This second transverse rod ends at least approximately at the vertical axis which, when projected on the plane of the film, goes through the point of intersection of the horizontal and vertical central axes on the film. The free end of this second transverse rod 6 carries an aiming rod 7 which is perpendicular to the said centre plane. This aiming rod 7 has markings 8, 9 and 10 and carries, at equal spacings on either side of the centre plane, aiming guides 11 and 12 which are included relative to the centre plane and towards the film holder by at least approximately equal angles of about 15°.

As seen in FIG. 1 the marking 9 is a projection at the intermediate of the transverse and aiming rods 6 and 7, for the aiming of an X-ray cone at an intersection of the horizontal and vertical center planes of a centrally retained X-ray film as seen in FIG. 4 with the aid of FIG. 1.

In FIGS. 2, 3 and 4, three essential positions of the film for odontological radiographs are shown, which are now required in connection with the explanation of the use of the device according to FIG. 1. In all three representations, the cone 13 of an X-ray source, such as is preferably used for odontological radiographs, is drawn in each case. As is known to all those skilled in the art, this cone 13 is fixed by means of joints to a hinged arm and it can be slewed over wide ranges in the horizontal direction and in the vertical direction and, additionally, it can also be tilted by marked angles.

According to FIG. 2, the roots of the lower teeth are to be depicted. For this purpose, a film 2 is inserted in a film holder 1 having at least two clamping brackets or clamping holders for two different positions of the film 1 relative to the centre plane which is now defined by the guide rod 5 and the transverse rods 4 and 6. In this case, this is thus done in such a way that the edge of the film is near the centre plane. This device is placed in the mouth of the patient and the latter is now required firmly to hold the bite wing 3 with his teeth. With the mouth closed, the point of intersection of the horizontal and vertical centre lines of the film can now be sighted, namely by adjusting the cone 13 to be parallel to the guide rod 5 and adjusting its tip to the marking 8. The radiographer is thus certain that the incidence of the X-ray will be exactly in the centre of the film.

In FIG. 3, it is intended to take a photograph of the roots of the upper teeth. As is known, the film plane of the film 2 must be tilted to the rear because of the curvature of the gums. This can be effected in a simple manner if the transition point between the film holder 1 and the bite wing 3 is designed in such a way that it can be elastically tilted. According to experience, the tilt angle relative to the vertical is about 30°. To keep the distortion of the image within limits, the axis of the cone 13 of the X-ray source is adjusted to be perpendicular to the bisector plane of the angle between a vertical plane and the film plane of the film 2. Thus, this corresponds to an angle $\alpha$ of about 15° relative to the centre plane formed by the guide rod 5 and the transverse rods 4 and 6.

In order to enable the cone 13 to be aligned accurately in an arrangement of this type, the aiming rod 7 also has aiming guides 11 and 12 in addition to the markings 8, 9 and 10. Adjustment can now be effected in two ways, namely the cone 13 is adjusted as in the preceding example and aligned parallel to the guide rod 5. Subsequently, the angle is read off on the angle marking of the X-ray device and 15° are added or subtracted, and the cone is adjusted to the corresponding aiming guide 11 at the calculated angle. Alternatively, the cone 13 is directly taken to the aiming guide 11 and the axis of the cone is aligned to the inclination of the aiming guide. If, additionally, care is also taken that the vertical centre plane passes through the cone in the direction of the aiming rod 7 and parallel to the guide rod 5, it is again possible, with the mouth closed, to obtain an image on the film which is directly in the centre.

The representation according to FIG. 3 was given for completeness' sake, and it should be possible also to derive all the settings for obtaining images of the crowns of the teeth from the examples described above.

FIG. 4 illustrates the taking of an X-ray photograph of the crowns of the lower and upper teeth with the aid of the marking 9.

FIG. 5 shows a lateral elevation of a film holder 1 having three pockets 14, 15 and 16. The crowns of the teeth can be depicted using a film 2 in the pocket 14, and the roots of the lower teeth and those of the upper teeth can be depicted using the film 2 in the pocket 15 or in the pocket 16 respectively.

According to the illustrative embodiment in FIG. 6, the bite wing 3 is not rigidly or elastically tiltably connected to the film holder 1 as in the examples described but, instead, the film holder is loose and can be joined to the bite wing 3 by a push-fit. For this purpose, a U-shaped profile piece 50 having three tranverse grooves 51, 52 and 53 is rigidly fixed to the film holder 1. The end 54 of the bite wing 3 is slightly pointed and hence conical. A clamped holding can be effected on insertion into one of the transverse grooves 51, 52 and 53. Additionally, a setting member 55 is rigidly connected to the end 54 of the bite wing 3. The setting member 55 is insertable into the U-profile and has the shape of a parallelogram, in which the angles are such that the bite wing 3 encloses an angle of at least approximately 60° with the film plane of the film 2.

In the illustrated preferred embodiments, the aiming rod 7 extends through, and is symmetrical relative to, the above mentioned horizontal center plane in which elements 3 to 6 extend.

The material for the manufacture of the device described can be selected in accordance with all possible aspects which appear appropriate for the particular purpose. Polystyrene would probably be very suitable for devices to be used only once. In contrast, if it is intended to use the device repeatedly, a sterilisable plastic must be used, such as, for example, polyethylene or Teflon. Moreover, the material can be rigid or it can be elastic and soft to the bite. All those skilled in the art will certainly also understand that the bite wing should be at most 3 mm thick, and it has been found that, in the direction perpendicular to the plane of the film, it should have a length of at least approximately 25 mm.

The embodiments of the film holders represented show pockets. It would, however, also be possible for the film holder to have the shape of a flat plate and to carry a layer of a water-resistant adhesive in order to fix the film immovably to the film holder.

I claim:

1. Device for holding X-ray film during the taking of radiographs of patients' teeth with X-rays emanating from a cone of an X-ray source, comprising in combination:
a bite wing extending in a horizontal center plane perpendicularly to an X-ray film plane, for retention of said device by patients' teeth;
an X-ray film holder carried by said bite wing and including means for retaining X-ray film centered relative to said horizontal center plane and alternatively vertically offset from said horizontal center plane;
a guide rod connected laterally to said bite wing and extending in said horizontal center plane perpendicularly away from said X-ray plane, for guidance of said X-ray cone;
an aiming rod extending in a vertical center plane of said centered and said vertically offset X-ray film;
a transverse rod extending in said horizontal center plane from said guide rod to said aiming rod, for mounting said aiming rod at a distance from said bite wing;
first means at said aiming rod for aiming said X-ray cone at an intersection of said horizontal and vertical center planes on said centrally retained X-ray film in the taking of radiographs of at least the crowns of upper and lower teeth; and
second means on said aiming rod for aiming said X-ray cone at an intersection of horizontal and vertical center lines of said vertically offset X-ray film in the taking of radiographs of root portions of said teeth.

2. Device as claimed in claim 1, wherein:
said aiming rod extends through, and is symmetrical relative to, said horizontal center plane.

3. Device as claimed in claim 1, wherein:
said second means include a marking on said aiming rod for aiming said X-ray cone at an intersection of horizontal and vertical center lines of said vertically offset X-ray film in the taking of radiographs of root portions of said teeth.

4. Device as claimed in claim 1, wherein:
said second means include an aiming guide on said aiming rod for aiming said X-ray cone at an intersection of horizontal and vertical center lines of said vertically offset X-ray film in the taking of radiographs of root portions of said teeth.

5. Device as claimed in claim 1, wherein:
said second means include aiming guides at opposite ends of said aiming rod for aiming said X-ray cone at an intersection of horizontal and vertical center lines of vertically offset X-ray films in the taking of radiographs of root portions of said teeth.

6. Device as claimed in claim 1, 2, 3, 4 or 5, wherein:
said first means include a projection at an intersection of said transverse and aiming rods.

7. Device as claimed in claim 1, 2, 3, 4, 5 or 6, wherein:
said film holder is fastened by a push-fit holder to the bite wing so that it can be pushed onto the latter.

8. Device as claimed in claim 1, characterised in that the aiming rod has markings which each correspond to a point of intersection of the horizontal and vertical centre lines of the film in any distinct position.

9. Device as claimed in claim 8, characterised in that one aiming guide in the form of a further rod is present at each of the two free ends of the aiming rod and that the aiming guides each enclose an angle of at least approximately 15° with the plane determined by the guide rod and transverse rod.

* * * * *